(12) United States Patent
Boyle

(10) Patent No.: US 8,519,356 B2
(45) Date of Patent: Aug. 27, 2013

(54) APPARATUS FOR STERILIZING THE INSIDE OF A CONTAINER

(76) Inventor: William P. Boyle, New Rochelle, NY (US)

( * ) Notice: Subject to any disclaimer, the term of this patent is extended or adjusted under 35 U.S.C. 154(b) by 0 days.

(21) Appl. No.: 13/442,383

(22) Filed: Apr. 9, 2012

(65) Prior Publication Data

US 2012/0261590 A1 Oct. 18, 2012

Related U.S. Application Data

(60) Provisional application No. 61/475,883, filed on Apr. 15, 2011.

(51) Int. Cl.
*A61L 2/10* (2006.01)
*A61L 2/24* (2006.01)
*A61L 2/08* (2006.01)

(52) U.S. Cl.
CPC ... *A61L 2/10* (2013.01); *A61L 2/24* (2013.01); *A61L 2/08* (2013.01)
USPC ............. 250/453.11; 250/454.11; 250/455.11

(58) Field of Classification Search
CPC ............. A61L 2/10; A61L 2/24; A61L 12/06; A61L 12/063; A61L 2/08; A61L 9/12; H01J 5/52
USPC ....................... 250/453.11, 454.11
See application file for complete search history.

(56) References Cited

U.S. PATENT DOCUMENTS

| | | | | |
|---|---|---|---|---|
| 1,788,906 A | * | 1/1931 | Brown | 250/453.11 |
| 1,984,457 A | * | 12/1934 | Buttolph | 250/455.11 |
| 2,384,778 A | * | 9/1945 | Whitman | 250/436 |
| 2,592,131 A | * | 4/1952 | Farrar | 250/455.11 |
| 2,844,727 A | * | 7/1958 | Maciszewski et al. | 250/438 |
| 3,906,236 A | | 9/1975 | Callahan | |
| 4,296,066 A | * | 10/1981 | Schenck | 422/24 |
| 4,317,041 A | * | 2/1982 | Schenck | 250/435 |
| 5,451,791 A | * | 9/1995 | Mark | 250/438 |
| 5,786,598 A | * | 7/1998 | Clark et al. | 250/455.11 |
| 5,916,439 A | * | 6/1999 | Oleskow | 210/198.1 |
| 6,433,344 B1 | * | 8/2002 | Salisbury et al. | 250/455.11 |
| 6,451,202 B1 | * | 9/2002 | Kuennen et al. | 210/136 |
| 6,491,868 B2 | * | 12/2002 | Kuennen et al. | 422/24 |
| 6,514,420 B2 | * | 2/2003 | Kuennen et al. | 210/748.11 |
| 6,569,319 B2 | * | 5/2003 | Kuennen et al. | 210/85 |
| 6,614,039 B2 | * | 9/2003 | Hollander | 250/504 R |
| 6,811,691 B2 | * | 11/2004 | Woodard et al. | 210/232 |
| 6,984,320 B2 | * | 1/2006 | Bartkus et al. | 210/238 |
| 7,166,216 B2 | * | 1/2007 | Woodard et al. | 210/232 |

(Continued)

FOREIGN PATENT DOCUMENTS

| | | |
|---|---|---|
| RU | 2026084 | 1/1995 |
| RU | 2296585 | 4/2007 |
| WO | WO 2010/133698 | 11/2010 |

*Primary Examiner* — David A Vanore

(74) *Attorney, Agent, or Firm* — Leason Ellis LLP

(57) ABSTRACT

A sterilization apparatus for sterilizing containers, such as plastic water bottles employs ultra violet (UV) light sterilization technology in a portable fashion. The apparatus is a standalone unit that is intended for residential use, is portable, and is specifically configured to receive and treat multiple sized bottles without additional add-ons. The apparatus positions and includes features to hold the bottle in a horizontal position within the housing of the apparatus such that the horizontally oriented UV bulb is disposed within the inside of the bottle.

20 Claims, 5 Drawing Sheets

(56) References Cited

U.S. PATENT DOCUMENTS

| | | | |
|---|---|---|---|
| 7,547,893 B1* | 6/2009 | Tantillo | 250/455.11 |
| 7,794,673 B2* | 9/2010 | Lucas et al. | 422/186.3 |
| 8,017,921 B2* | 9/2011 | Kemp et al. | 250/455.11 |
| 2002/0011434 A1* | 1/2002 | Kuennen et al. | 210/97 |
| 2006/0231470 A1* | 10/2006 | Hatch et al. | 210/198.1 |
| 2007/0075268 A1* | 4/2007 | Harris | 250/455.11 |
| 2009/0316412 A1* | 12/2009 | Yeh et al. | 362/285 |
| 2011/0305597 A1* | 12/2011 | Farren | 422/24 |
| 2012/0068088 A1* | 3/2012 | Durkin | 250/492.1 |
| 2012/0121457 A1* | 5/2012 | Farren | 422/3 |
| 2012/0261590 A1* | 10/2012 | Boyle | 250/453.11 |

\* cited by examiner

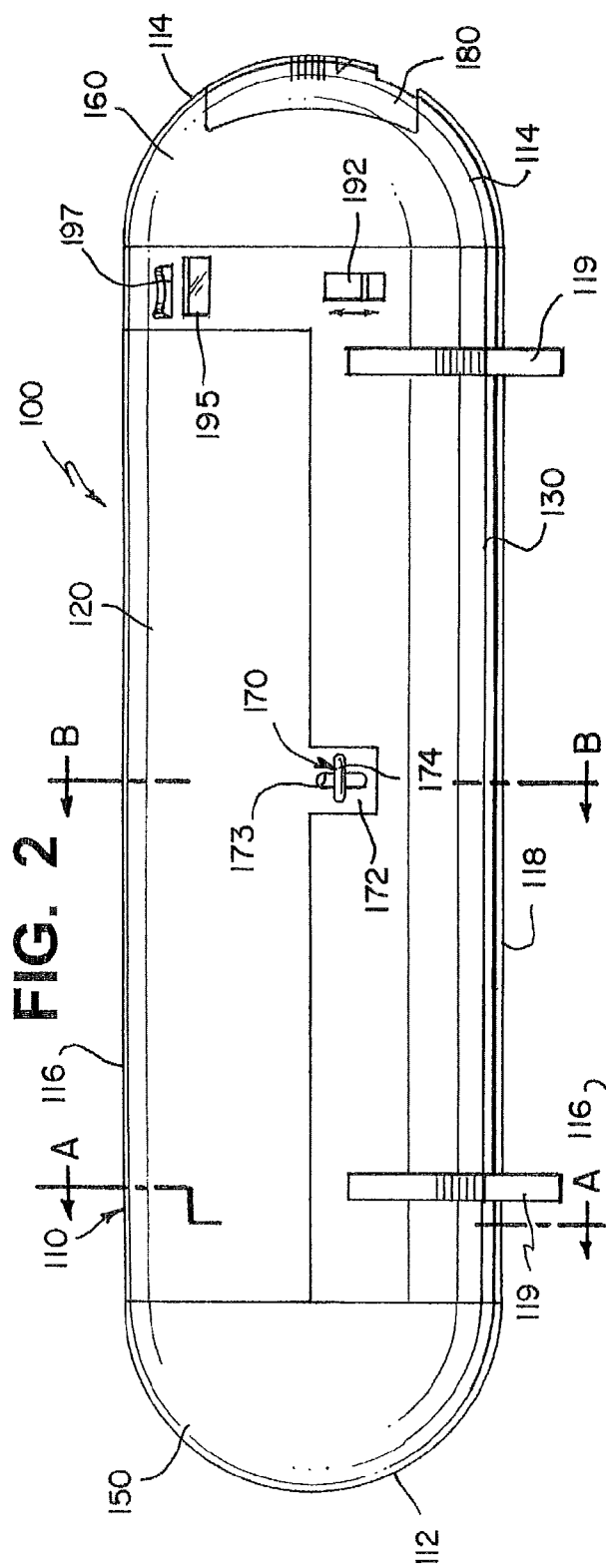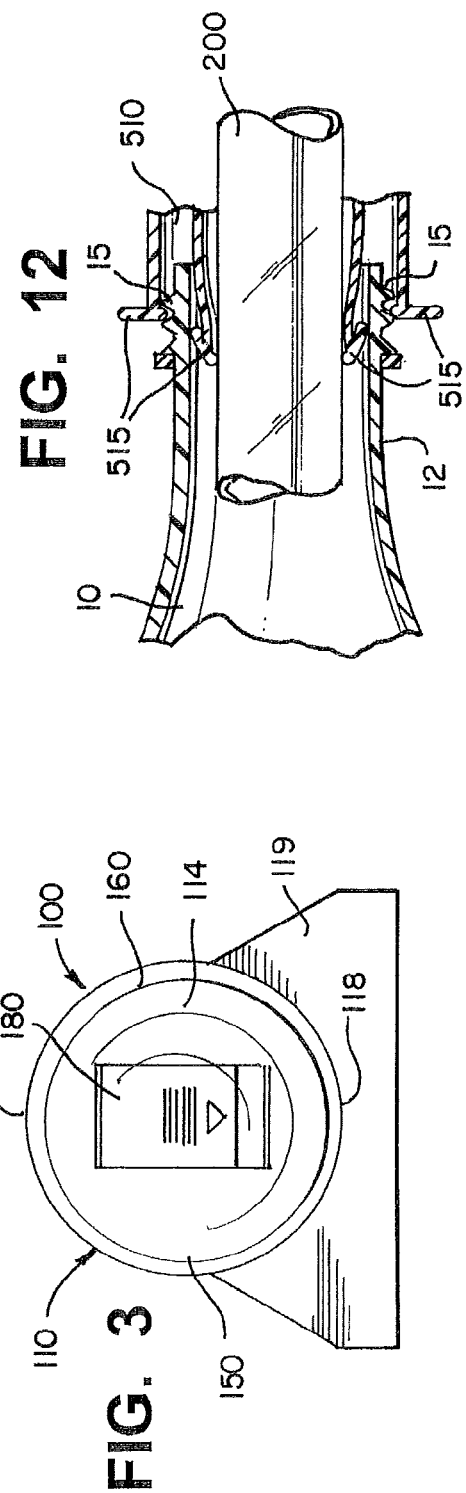

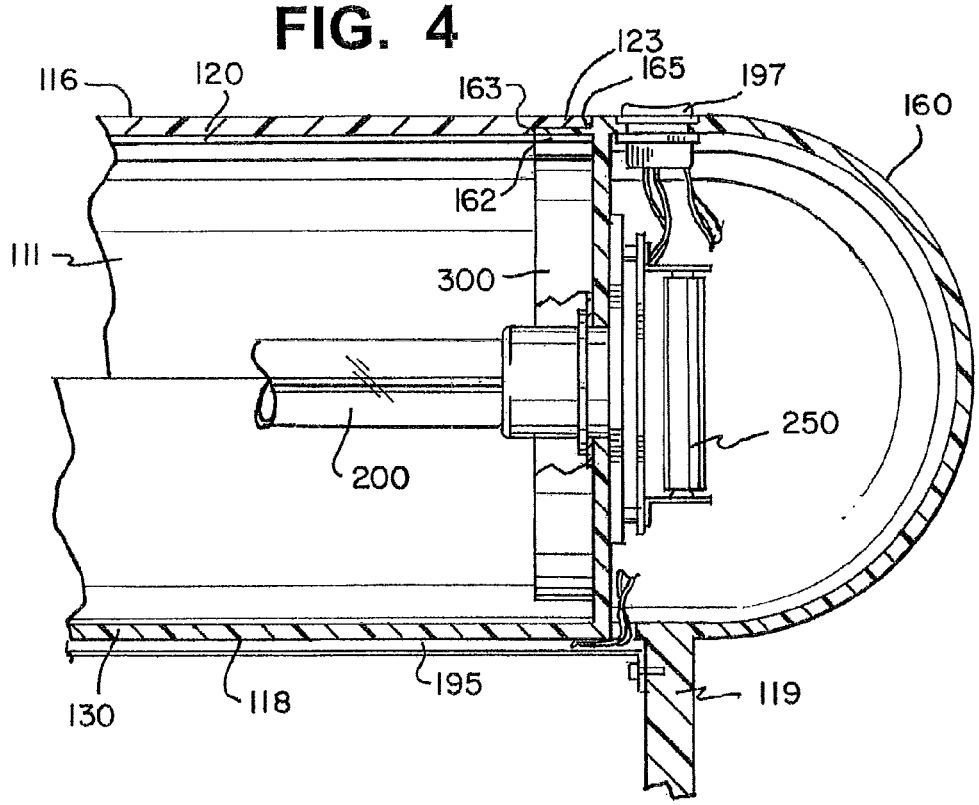
FIG. 4
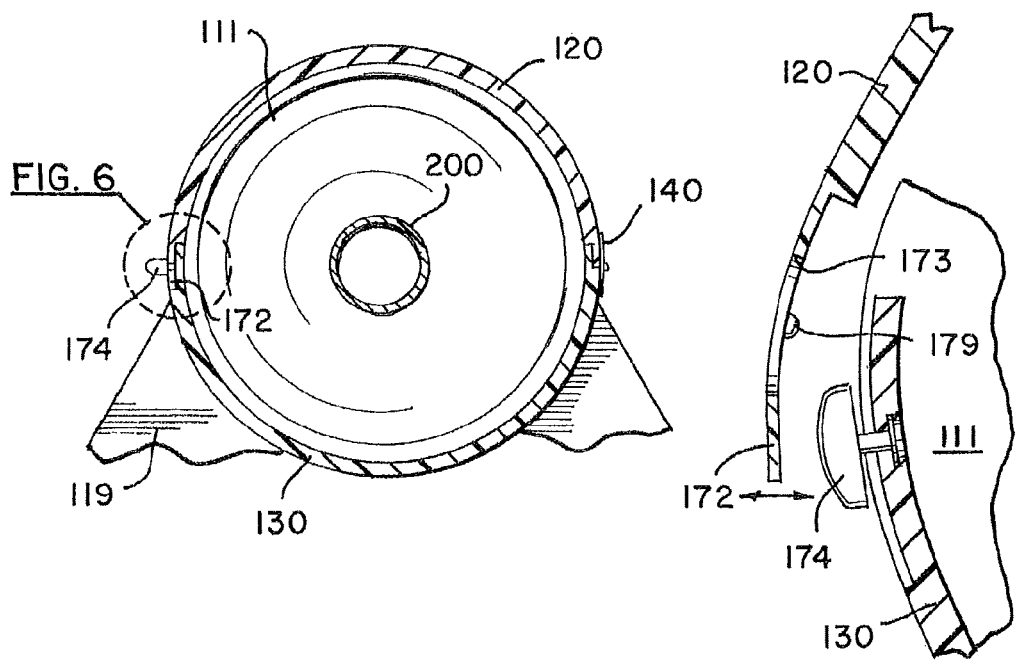
FIG. 5          FIG. 6

APPARATUS FOR STERILIZING THE INSIDE OF A CONTAINER

CROSS-REFERENCE TO RELATED PATENT APPLICATION

The present application claims priority to and the benefit of U.S. Patent Application No. 61/475,883 filed Apr. 15, 2011, which is hereby incorporated by reference in its entirety.

TECHNICAL FIELD

The present invention relates to an apparatus and method for sterilizing containers, and in particular, for sterilizing the inside of water bottles or the like using a standalone unit that is intended for residential use.

BACKGROUND

There are a tremendous amount of food and beverage products that are stored in containers that are meant for single use and are then disposed of after use. These products include food stuffs as well as various beverages. The products can be stored in containers formed of different materials including aluminum cans and most commonly, plastic containers that can hold solids, semi-solids or liquids like beverages.

One of the largest subcategories is the field of bottled beverages. In particular, bottled water has become a large global industry. As with other products, when the containers of bottled water are reused one or more times, the water begins to exhibit a tarnished taste due to build up of foreign material along the inner walls of the container. This foreign material can include potentially dangerous bacteria build-up. In addition and unfortunately, one of the ill effects of the increasing growth of bottled water is the increasing waste that is generated and in particular, the plastic bottles represent waste products. While bottled water container can be recycled, many individuals are simply too lazy to recycle and/or their locales simply do not have a widespread recycling program. In fact, only about 25% of products that could be recycled are actually being recycled and when there are many billions of discarded bottled in just the U.S. each year, the number that end up in landfills is staggering.

Bottled water and similar products are also quite costly relative to the cost of tap water which in many or most households can have an acceptable to good taste and thus represents a source of drinkable water. For example, even if the local water supply has unfavorable characteristics, such as being "hard", there are simple treatment devices that can be attached to faucets for treating the water and making it acceptable for, residential consumption.

There are many different techniques and devices for sterilizing surfaces and/or objects. One conventional sterilization method involves heating an object to high temperatures using dry heat, boiling water, and steam paths. These methods, however, consume a substantial amount of time and energy, and commercial apparatus can be costly. Moreover, the time-consuming nature of heat sterilization makes the method inconvenient in many situations including in a normal residential setting. The method is commonly used for heating tools (medical instruments) that are wrapped in special paper that indicates when the sterilization is complete. This type of device is typically slow, with sterilization taking on the order of up to an hour, although recent technology has cut the sterilization times down to 10 minutes or so. Steam sterilization using an autoclave is probably the most widely used type of device for sterilization. Similar to the dry heat method, instruments are packed in special paper. The package is then placed in a high pressure/high temperature steam bath. Steam penetrates all surfaces of the instrument. At the end of the process, the steam is removed from the chamber and the device comes out dry. Autoclaving, however, is also slow and can be detrimental to some plastics. Finally, boiling and pasteurization can be used when a high degree of sterilization is not needed; however, both techniques require 10 to 20 minutes to complete.

In addition to heat-based techniques, chemical sterilization can be used in heated vapor systems as well as in cold systems. This method offers shorter times, but can be more destructive to plastics. Also, the chemical solutions used may be highly corrosive and toxic.

Most common bacterial and cellular organisms that can cause sickness and disease in humans can be killed with moderate doses of ultraviolet light (e.g., UV light having a wavelength between about 200 nm and 280 nm (e.g., 250-260 nm). The use of (ultraviolet) UV light to sterilize work surfaces, equipment and the like require an external source of power, such as a wall socket, to produce a continuous stream of UV light. UV treatment has been disclosed in a variety of application including large scale plant applications where bottles that are part of a mass bottle filling process are first sterilized with UV light before the contents are delivered thereto. This type of machinery is industrial based and is thus on a large scale. There have been attempts to create a portable sterilizing apparatus to treat containers; however, these attempts have been mostly in the baby care industry and in particular, deal with sterilization of baby bottles, bottle nipples (teats), pacifiers, teething rings, etc. can be placed for sterilization by pulses of UV radiation. The problem with the above UV sterilizers is that they are either not suitable for use for sterilizing other types of common containers (bottles) that are more adult oriented and in particular, are not suitable for use with water bottles and the like.

SUMMARY

The disclosed present invention, which involves the use of ultra violet (UV) light sterilization technology in a portable fashion, exceeds the convenience and requirements of the marketed sterilization units, which use cold water, electrical and/or microwave means to sterilize bottles, such as water bottles. The disclosed apparatus is a standalone unit that is intended for residential use, is portable, and is specifically configured to receive and treat multiple sized bottles without additional add-ons. The apparatus positions and includes features to hold the bottle in a horizontal position within the housing of the apparatus such that the UV bulb is disposed within the inside of the bottle. A number of different control features and safety features are likewise provided and disclosed herein.

In one embodiment, an apparatus for sterilizing an inside of a container includes a housing having a first part and a second part that define an interior. The first part is movable relative to the second part between an open position and a closed position in which the first and second parts are sealed. The housing includes a first end portion that closes off a first end of the housing and is attached to the first part such that the first end portion and the first part move in unison between the open and closed positions. The housing also includes a second end portion that closes off a second end of the housing and is attached to the second part and remains in a fixed position in the open and closed positions. The apparatus also includes a UV bulb disposed horizontally within the interior and spaced above a floor of the second part.

In addition, the apparatus includes a first retaining member for holding a neck portion of the container. The first retaining member is disposed about the UV bulb at one end thereof and having a plurality of concentric slots for accommodating different sized neck portions to permit the UV bulb to be received within an interior of the container. A support is disposed along the second part, wherein the first retaining member and support are configured to hold the container in an least substantially horizontal orientation within the interior. A power source operatively connected to the UV bulb and to a controller that provides control over the activation of the UV bulb.

These and other aspects, features and advantages shall be apparent from the accompanying Drawings and description of certain embodiments of the invention.

BRIEF DESCRIPTION OF THE DRAWINGS

FIG. 2 is a side elevation view of the apparatus in a closed position;

FIG. 3 is an end elevation view of the apparatus;

FIG. 4 is a cross-sectional view of an end portion of the apparatus of FIG. 1;

FIG. 5 is a cross-sectional view taken along the line B-B of FIG. 2;

FIG. 6 is an enlarged cross-section view of a latch assembly taken from FIG. 5;

FIG. 12 is a close-up cross-sectional view of a neck portion of the bottle in engagement with the means of FIG. 11 for holding the bottle in place.

DETAILED DESCRIPTION OF CERTAIN EMBODIMENTS OF THE INVENTION

Figure 1:
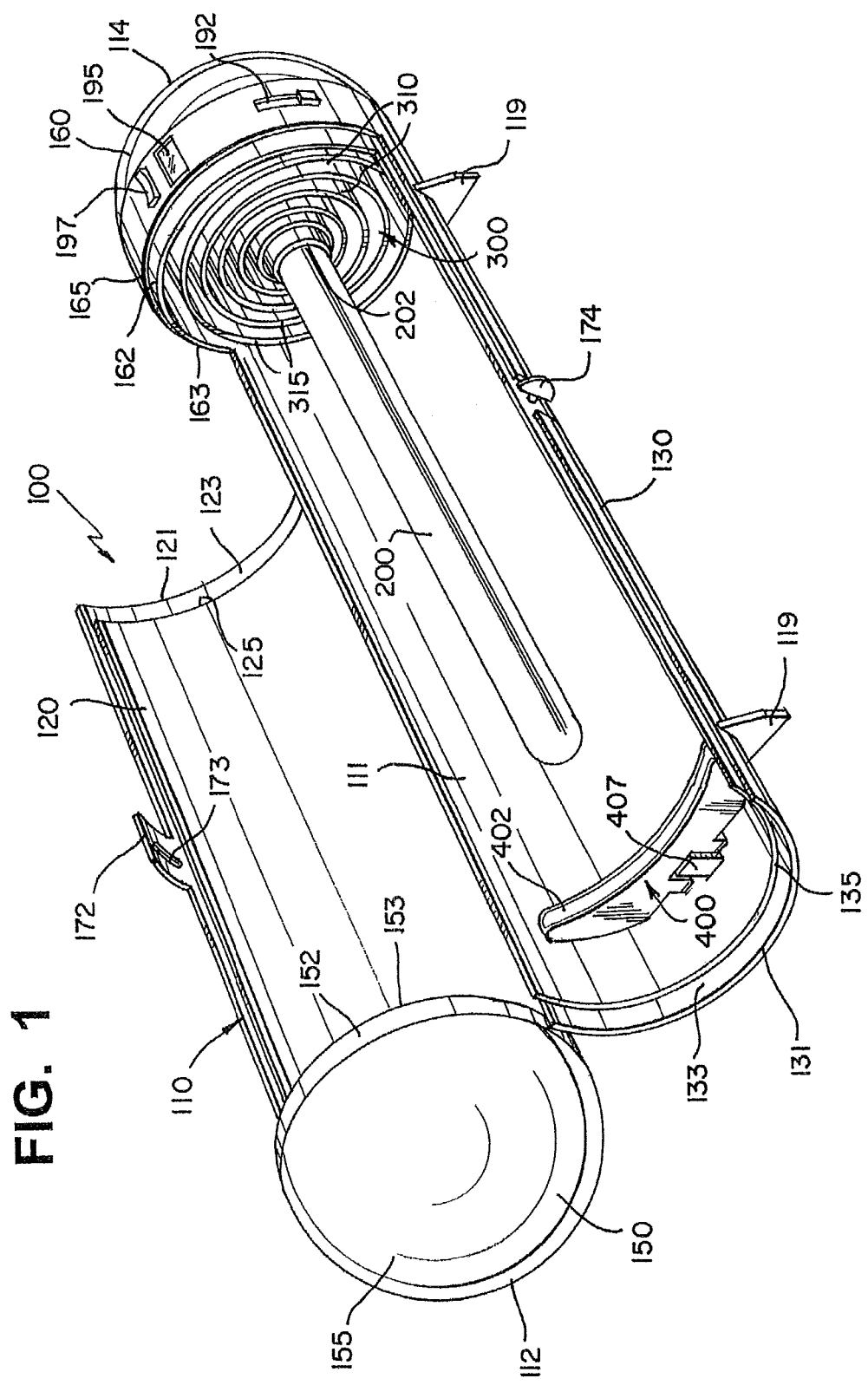
FIG. 1 is a side perspective view of an apparatus in accordance with one embodiment of the present invention in an open position.
Figure 7:
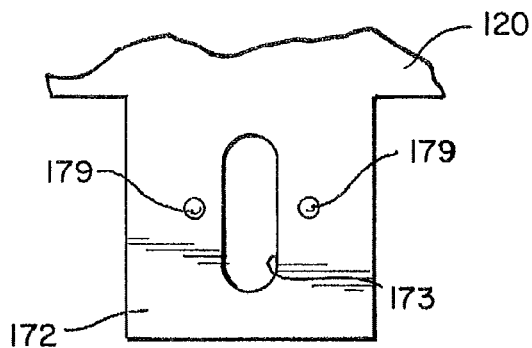
FIG. 7 is an elevation view of a first part of the latch assembly.
Figure 8:
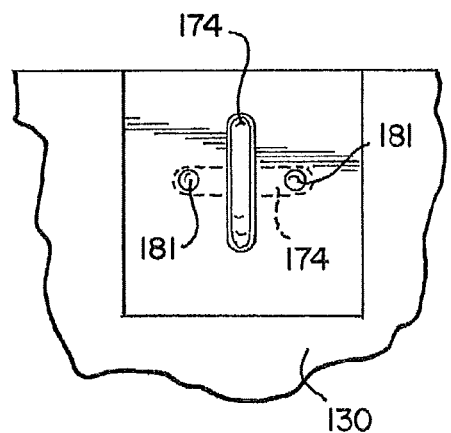
FIG. 8 is an elevation view of a second part of the latch assembly.

It should be readily apparent to one of ordinary skill in the art that the examples disclosed herein below represent exemplary examples only, and that other arrangements are possible and are embraced by the present invention.

Now referring to FIGS. 1-8, an apparatus 100 for cleaning (sterilizing) an inside of a container 10 is shown. More specifically, the apparatus 100 is particularly suited for sterilizing the inside of a bottle 10 after the contents of the bottle 10 have been consumed by an individual. The apparatus 100 is thus intended to permit a consumer to reuse a bottle, at least several times, that would otherwise be discarded and potentially end up in a landfill as waste. As such, the apparatus 100 is environmentally friendly. As described herein, the apparatus 100 is intended for residential use by consumers and is therefore, configured for use in a residence (e.g., on a countertop or the like). As such, the apparatus 100 is sized and shaped for convenient use and is configured to receive a single bottle (container) 10. Thus, after use of a single bottle 10, an individual can place the used bottle 10 into the apparatus 100 and activate the sterilization means so as to sterilize the inside of the bottle. Once sterilized, the cleaned (sterilized) bottle 10 can then be used again as by filling the bottle with a liquid, such as refilling it with water, etc. This produces an immediate savings to the consumer since a refill of tap water is only costing cents, while buying an extra bottle of water cost anywhere from 50 cents to more than 1 dollar (i.e., hundreds of times more costly than using tap water).

The apparatus 100 includes a housing 110 that is configured to sealingly receive and contain the bottle 10 and also contains the active and electronic components of the apparatus 100. In the illustrated embodiment, the housing 110 includes a first end 112 and an opposing second end 114 and includes a top surface 116 and an opposing bottom surface 118.

The housing 110 is actually formed of several parts or sections that permit the housing 110 to move between an open position for receiving the bottle 10 and a closed position in which the bottle 10 is sealingly contained therein and the apparatus 100 is ready for use. For example, the housing 110 can contain a first (top) section 120 and a second (bottom) section 130. The top section 120 is coupled to the bottom section 130 in such a way that the top section 120 moves relative to the bottom section 130 and more specifically, the top section 120 opens and closes relative to the bottom section 130. Thus, in this embodiment, the bottom section 130 is a fixed member, while the top section 120 is a movable member in the form of a cover.

In accordance with the illustrated embodiment, the top section 120 is pivotally attached to the bottom section 130 as by a hinge 140 or the like. The top section 120 can thus pivot between a fully opened position (FIG. 1) and a fully closed position (FIG. 2). The top section 120 does not extend from the first end 112 to the opposite second end 114 but only partially extends therebetween. As shown in FIGS. 1 and 2, the top section 120 also includes and incorporates a first end portion 150 at the first end 112 of the housing 110. As a result and as described in more detail below, the first end portion 150 sealingly closes off the first end 112 of the housing and moves in unison with the top section 120. Therefore, the opening of the top section 120 also results in the simultaneous movement (opening) of the first end portion 150 so as to open the first end 112 of the housing 110 and permit lateral reception of the bottle 10 as described herein.

The illustrated top section 120 has an arcuate shape and can be semi-circular in shape. As shown, when the top section 120 is semi-circular in shape, at least a portion of the bottom section 130 is likewise semi-circular in shape to permit the two part to mate together to form an at least generally cylindrically shaped object with rounded or planar ends. The top and bottom sections 120, 130 mate in a sealed manner. The shapes of the top and bottom sections 120, 130 are not critical so long as they sealingly mate together and capture and hold the bottle 10.

The first end portion 150 is constructed to sealingly mate with the bottom section 130 and can be in the form of a planar disk or, as shown, can be in the form of a dome-shaped structure. In the illustrated embodiment, the dome-shaped end portion 150 has an arcuate-shaped (e.g., semi-circular shaped) flange 152 at an open end 153 thereof. The opposite end 155 of the first end portion 150 is closed and not accessible. An open end 131 of the second section 130 has a complementary recessed area or track 133 that is intended to receive the flange 152 and seal off an interior 111 of the housing 110 in such a way that energy emitted in the interior 111 is fully contained therein and the user is not exposed to such energy. The track 133 can likewise be semi-circular in shape and is defined by a shoulder 135 (e.g., a right angle shoulder spaced from the end of the bottom section 130). In the fully closed position, an outer edge 153 of the flange 152 seats against the shoulder 135, thereby sealing the interior 111.

The bottom section 130 can have a similar construction in that the bottom section 130 is not completely open at ends 112, 114 but instead, the bottom section 130 is also integrally attached to a second end portion 160 that closes off the second end 114 of the housing 110. The second end portion 160 can have a flat planar end or, as shown, it can have a dome-shape. The second end portion 160, as described below, houses a number of active parts, including electronics, of the apparatus 100 and thus, remains fixed in place, while the first end portion 150 that does not include active components, is movable.

Like the dome-shaped first end portion 150, the dome-shaped second end portion 160 includes an arcuate-shaped (e.g., semi-circular shaped) flange 162 at an end 163 thereof. The opposite end 165 of the second end portion 160 is closed and not accessible. An open end 121 of the first section 120 has a complementary recessed area or track 123 that is intended to receive the flange 162 and seal off an interior 111 of the housing 110. The track 123 can likewise be semi-circular in shape and is defined by a shoulder 125 (e.g., a right angle shoulder spaced from the end of the top section 120). In the fully closed position, a shoulder 165 of the flange 162 seats against the shoulder 125, thereby sealing the interior 111.

Thus, in the illustrated embodiment, the bottom section 130 include a semi-circular part that extends from the second end portion 160 and similarly, the top section 120 includes a semi-circular part that extends from the first end portion 150. When the top and bottom sections 120, 130 mate together and are in the closed position, these two semi-circular parts are in engagement with one another. For example, the semi-circular portions can have lips (flanges) at select edges for reception in an undercut area formed along edges of the opposing semi-circular portion.

It will therefore be understood and appreciated that unlike traditional devices, the apparatus 100 of the present invention is designed so that not only a portion of a side wall (section 120) opens to permit access to the interior 111 but also one end portion (first end portion 150) of the housing 110 is integrally attached to the side wall section 120 so that both open simultaneously so as to open the interior 111 not just along the side wall but also at one end of the apparatus 100.

To securely couple or lock the first and second sections 120, 130, a latch assembly 170 can be provided with a latch tab 172 being associated with the top section 120 and extending outwardly from one edge thereof and a locking tab 174 being associated with the bottom section 130 and extending outwardly near one edge thereof. The latch tab 172 has a slot 173 formed therein for receiving the locking tab 174 when the locking tab 174 is in a first position (vertical position). Once the locking tab 174 is received within the slot 173, the user locks the apparatus 100 by rotating the locking tab 174 so that it is no longer in registration with the slot 173. For example, the user simply rotates the locking tab 174 so that it is no longer vertically oriented (e.g., the locking tab 174 is in a horizontal position). The locking tab 174 is thus rotatably attached to the second section 130 and can include a shaft and head portion. It will be appreciated that any number of other locking mechanisms can be employed.

The housing 110 can have feet 119 or the like to support it in a level, horizontal manner across a planar support surface.

In accordance with the present invention, the sterilization means is in the form of ultraviolet radiation in a wavelength range (e.g. 200-300 nm) that achieves an optimal extermination of the germs and micro-organisms that are on the interior surface of the bottle 10. In particular, a UV source, in the form of a bulb or lamp, 200 is disposed within the interior 111. The UV light source 200 can be a tube lamp manufactured from glass. The UV light source can be constructed to emit UV light having a wavelength in the range of 100 nm to 300 nm, which is commonly called UV-type C radiation. The UV bulb 200 can be covered by a protective cover, such as a protective sheath, through which UV radiation can penetrate to prevent accidental breakage of the bulb 200. The protective cover will prevent any contact with the bulb surface, which is desirable to prevent contamination by the bulb and/or the bulb being fouled.

The UV bulb 200 has an elongate construction and includes a first end 202 that is fixedly attached to the second end portion 160 and an opposite second end 204 that represents a free end. The UV bulb 200 is disposed within the interior 111 of the housing 110 and is oriented in a horizontal manner in that the UV bulb 200 extends along a length of the apparatus between the ends 112, 114. The bottle 10 is received within this space.

As described below, the UV bulb 200 is supported at the first end 202 such that the UV bulb 200 is suspended over the bottom section 130. In other words, a space is formed between the UV bulb 200 and an arcuate shaped floor of the apparatus 100 which is defined by the top surface of the bottom section 130.

The UV bulb 200 does not extend the entire length of the bottom section 130 but instead terminates at a point prior to the open end. The UV bulb 200 is received within the open interior of the bottle 10 and is therefore sized accordingly. In other words, the UV bulb 200 is received within an open neck portion 12 of the bottle 10 into the larger main body section 14 thereof.

While the UV bulb 200 is shown to have a round shape, this is merely one exemplary shape for the UV bulb 200 and other shapes are equally possible, such as a more flat shape (rectangular shape).

The UV bulb 200 is powered by a power source 250 (FIGS. 4 and 8) which preferably is in the form of one or more batteries that are housed within the hollow interior of the second end portion 160. As shown in FIGS. 2 and 3, the second end portion 160 can include a battery compartment that is accessed through a removable or openable door 180. For example, the door 180 can be a slidable door that opens by sliding the door 180 is a predetermined direction, such as in the direction indicated by the arrow in the figures. Once removed, the batteries are accessible and can be removed or can be recharged as by connecting the power source (batteries) to a conventional electric outlet or other charging means using a power cable, etc. Any number of different types of power sources can be used in the present invention so long as they are capable of powering the UV bulb 200 and the other electronics for a reasonable amount of time to permit multiple uses of the apparatus 100 before recharging is needed.

The energy required to kill microorganisms is dependent on the UV light source intensity factor (intensity by Wang rating) and exposure time (seconds) to said energy. This energy is measured in microwatt seconds per square centimeter ($\mu$Watt Seconds/cm$^2$). UV radiation is emitted predominately perpendicular to the surface of the lamp (bulb). Recommended dosages of UV radiation for an average 90% kill/inactivation of most bacteria and virus range from 2,000 to 8,000 µWatt Seconds/cm². Preferably, the apparatus 100 of the present invention achieves an at least 90% average kill/inactivation of bacteria/viruses. The UV light source provides sufficient intensity and duration to achieve this. Desirably, the apparatus 100 provides UV radiation that is a multiple of the minimum dose to achieve this 90% kill/inactivation. For example, it is desirable that the dose deliverable during a sterilization cycle is at least 2 times, suitably at least 3 times, for example at least 4 times, such as at least 8 times, desirably at least 10 times that required to achieve an at least 90% average kill/inactivation.

Figure 13:
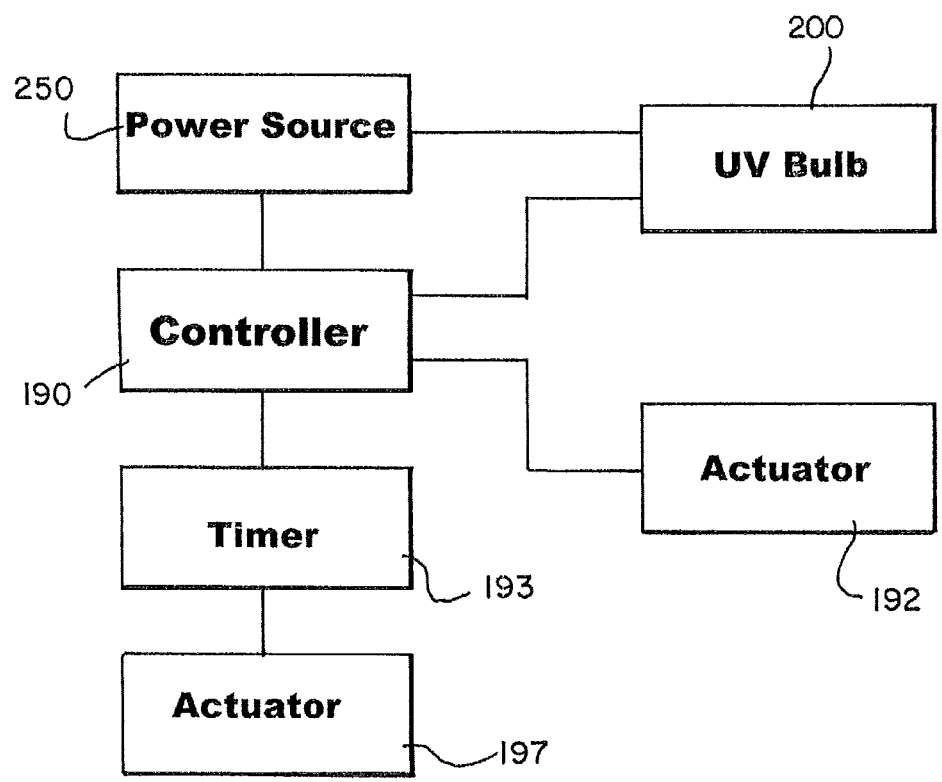
FIG. 13 is a schematic showing one operating system of the apparatus of FIG. 1.

As mentioned above, the second end portion 160 also houses other active/electronic components of the apparatus 100. As shown in FIG. 13, a controller 190 is included and is operatively connected to other working components of the apparatus 100, such as the UV lamp 200 and is also connected to the power source 250. The controller 190 can include a printed circuit board (PCB) that is connected to the power source 250 and the UV lamp 200 and is programmed to permit operation of the UV lamp 200. The PCB thus directs power from the power source to the UV bulb.

The controller 190 includes an actuator 192 for controlling operation of the apparatus 100 and while the figures show the actuator 192 as a simple switch or button, any number of different types of actuators can be used. In the simplest form, the actuator 192 is merely an on-off switch. However, other embodiments are possible and preferred in which the actuator permits different operating modes to be selected as by positioning in a prescribed position.

The controller 190 can also include a timer 193 that permits the UV actuation time to be controlled and set and/or selected using conventional controls. The timer can be controlled with a separate actuator 197, such as a button or switch. The timer 193 allows the user to set the time for which the apparatus 100 emits UV light or for automated cycles displays the cycle time, for example by counting down from or counting up to a specific time. LED lights can be used to indicate to the user when the programmed time has finished by color change, turning on/off, changing intensity, etc. In addition, the apparatus 100 can also have an aural indicator either in addition to or in place of LED lights.

A timer display 195 (e.g., LED) can be provided for displaying the above information, as well as other information, including operating modes and the like.

The actuator 192 can also be an electronic, programmable actuator in which the user can program different operating modes with a keypad (not shown) or the like. In addition, the timer 193 can be programmable to permit the user to select a desired UV actuation period.

The circuit board and electronics are separated from the interior 111 as shown. In particular, the circuit board and electronics are disposed within the hollow interior of the second end portion 160.

In addition, the surfaces of the interior 111 of the apparatus 100 can be coated with a reflective surface which allows the UV light to be reflected inside the interior 111 when activated.

The apparatus 100 can also have a means for ensuring that the cover (top section 120) of the apparatus 100 is fully closed before the UV bulb 200 can be activated. For example, a pair of conductive contacts can be provided with one being disposed on the top section 120 and the other on the bottom section 130. The contacts can be located in any number of different locations so long as when the top section 120 is closed relative to the bottom section 130, contact is made between the two contacts and a signal is generated and delivered to the printed circuit board. One contact (e.g., the contact associated with the bottom section 130) is electrically connected to the printed circuit board for delivering the signal thereto when the cover (top section 120) is closed. One location for placement of the contacts is at or near the flange 162 of the second end portion 160 and the track 123 of the top section 120. In addition, the contacts can be part of the latch/lock assembly such that the UV lamp 200 is not permitted to be actuated until the cover (top section 120) is shut and the latch/lock is in a locked position.

It will be appreciated that other sensor arrangements can be used to detect when the top and bottom sections 120, 130 are secured to one another or at least in sealed engagement with one another. As mentioned above, the controller can be programmed such that the UV bulb 200 cannot be operated (i.e., no power is delivered thereto) until the housing 110 is completely sealed and in the closed position.

For example, FIGS. 5-8 show another sensor arrangement in which the sensors are incorporated into the latch assembly 170. For example, the latch tab 172 can include a pair of protrusions 179 that are located on either side of the slot 173. The bottom section 130 includes depressions 181 that are formed on either side of the pivotal locking tab 174. The depression 181 can include contacts that are electrically connected to the controller 190 by means of wires that extend along a chase 195 formed below the section 130. The protrusions 179 contact the contacts in the depressions 181 and upon making contact and this results in a signal being sent to the controller to indicate that the two sections 120, 130 are in the closed position and operation of the UV bulb 200 is permitted.

In addition, the controller of the present invention can be configured so that when the top section 120 is shut and sealed relative to the bottom section 130, the UV bulb 200 can be automatically operated in that power is delivered to the UV bulb 200.

As is well known, container 10, such as water bottle, has neck portion 12 that forms an entrance into the larger main body section 14 that stores the liquid, in this case water. Typically, the neck portion 12 has external threads 15 or the like to permit a cap (not shown) to be attached. An opposite end 16 of the bottle 10 is the closed end thereof.

In accordance with the present invention, the container 10 is disposed and held within the interior 11 such that the UV bulb 200 is disposed within the hollow interior of the container 10. Thus, the container 10 is oriented horizontally within the interior 11 much like the UV bulb 200 and in order for the container 10 to remain spaced from the UV bulb 200, the housing 110 has a number of members or features to support the container 10 at or near both of its ends. More specifically, the apparatus 100 includes a means for holding and supporting different sized necks 12 of different bottles 10, such as different shaped or different sized water bottles. In other words, the apparatus 100 includes a first bottle (container) holder (retaining) member 300 that is located near or is part of the second end portion 160.

The first bottle holder member 300 is constructed to receive and mate with multiple sized necks 12 of different respective bottles 10 to allow the apparatus 10 to be used universally with a number of different bottles 10 without requiring modification or retrofitting thereof. The illustrated first bottle holder member 300 is in the form of a plurality of concentric seals (rings) 310 that are formed of a resilient material, such as rubber or plastic, that is designed to receive and seat against the neck portion 12. For example, the seals 310 can be in the form of a plurality of O-rings or other structures that have different diameters that progressively increase.

The seals 310 surround the UV bulb 200 and therefore, the UV bulb 200 is disposed within the innermost ring (seal) 310. It will thus be appreciated that between any two adjacent rings 310 an annular shaped track (slot) 315 is formed. It is within this track 315 that the neck 12 of the bottle 10 is disposed such that the UV bulb 200 and one or more inner rings 310 (relative to the neck) are disposed within the interior of the neck portion 12 of the bottle 10 and one ring 310 sealingly seats against and around the exterior of the neck portion 12. Thus, one ring 310 seats against the interior surface of the neck portion 12 and one ring 310 seats against the exterior surface. By being received and frictionally held between rings 310, the bottle 10 can be suspended and held in place around the UV bulb 200. The material from which the rings 310 are formed promotes an intimate fit of the neck portion 12 within the member 300, thereby causing the bottle 10 to be suspended above the bottom section 130.

It will be appreciated that the different concentric tracks 315 define different receiving spaces for different sized bottles 10, thereby allowing different sized bottles 10 to be held in place by the member 300 in such a way that the bottle 10 is held substantially horizontal and about the UV bulb 200.

Figure 9:
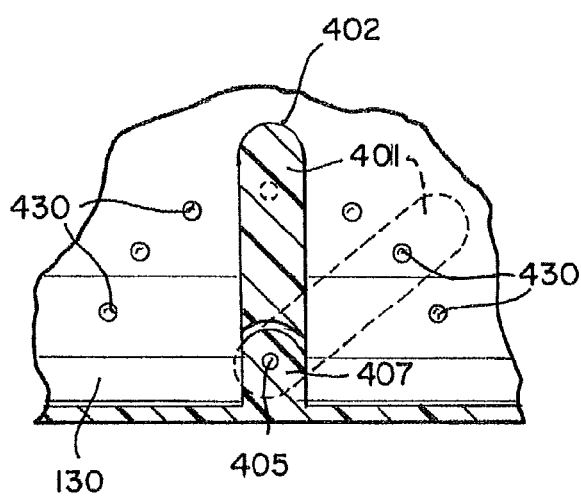
FIG. 9 is a partial side view of a portion of the apparatus showing an adjustable member for supporting one end of the bottle.
Figure 10:
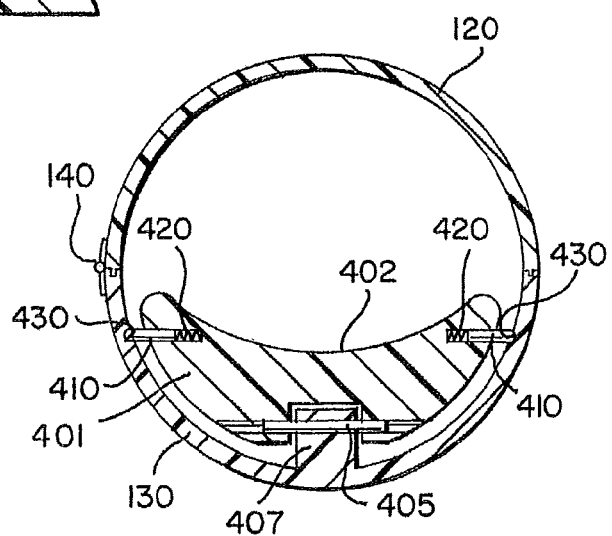
FIG. 10 is cross-sectional view taken along the line A-A of FIG. 2.

The apparatus 100 also includes a second bottle holder member in the form of a positionable/adjustable riser 401 that supports another portion (near end 16) of the bottle 10. The adjustable support member 401 is located along the bottom section 130. As shown in FIGS. 9 and 10, in one embodiment, the support member 401 is in the form of a pivotal riser 400 that is pivotally to the bottom section 130. The riser 401 has a top arcuate edge 402 that is complementary to the traditional curved shape of the bottle 10 to allow seating of the bottle 10 within and against the top edge 402. The member 401 can be pivotally attached to the arcuate shaped wall of the bottom section 130 to permit the member 400 to be set at different positions in which the top edge 402 is located at different distances from the floor of the bottom section 130 so as to accommodate bottles 10 having different diameters.

For example, the riser 401 can pivot about an axle 405 that is coupled at its ends to the curved wall of the bottom section 130 or as shown, the axle 405 can extend through a bottom protrusion 407 that is part of the bottom section 130. The riser 401 thus pivots about the axle 405. To lock the riser 400, a pair of locking pins 410 is used. Each pin 410 is located along sides of the riser 400 and is biased within a slot formed in the riser 401. More specifically, a biasing member 420, such as a spring, is disposed within a slot formed in the riser 401 and applies an outward biasing force against the pin 410. Along the side wall of the bottom section 130, a plurality of spaced openings 430 are formed and are sized and shaped to receive the pins 410. The pins 410 are naturally biased outwardly and therefore, once the pins 410 are in registration with one set of the openings 430, the pins 410 seat therein. The openings 430 preferably have cam surfaces such that when the riser 400 is moved, the pins 410 ride along the cam surfaces to cause retraction of the pins 410 resulting in the pins 410 being disengaged from the openings 430.

The riser 401 can thus be set at the preferred angle/location by placing the pins 410 in the corresponding openings 430. Once locked in place, the riser 401 supports this end 16 of the bottle 10. In combination with the member 300, the riser 401 permits the bottle 10 to be horizontally supported within the interior 111 around but not in contact with the UV bulb 200.

It will be appreciated that any number of different types of adjustable risers 401 can be used. For example, a plurality of risers 401 can be provided in a kit and can be coupled to the bottom section 130 using a mechanical attachment. For example, the bottom edge of the riser 401 can include a male or female coupling member that mates with a complementary female or male coupling member that is part of the floor of the bottom section 130. A snap-fit type attachment can be thus provided between the riser 401 and the bottom section 130. This allows the user to easily interchange riser 401 and simply click and lock the proper riser 401 in place along the floor in view of the size and shape of the bottle 10 to ensure that the end 16 of the bottle 10 is properly supported (e.g., the bottle 10 is disposed horizontally within the bottle 10).

Figure 11:
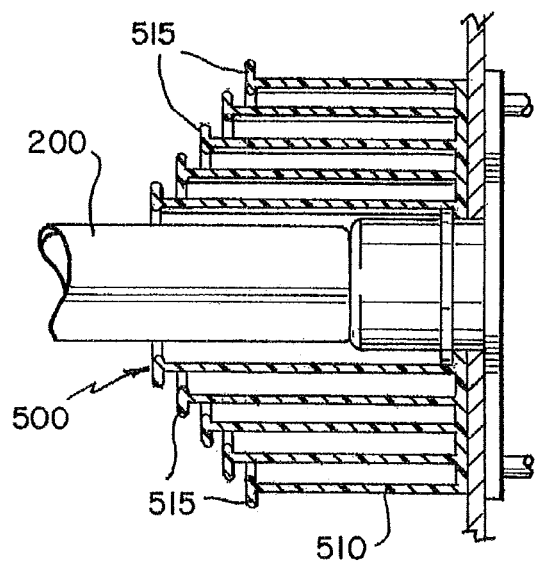
FIG. 11 is a side cross-sectional view of a portion of the apparatus showing an alternative means for supporting a neck portion of a bottle.

Now referring to FIGS. 11 and 12 in which a neck support member 500 according to another embodiment is shown. The neck support member 500 is formed of a plurality of flexible fingers 510 that are disposed concentrically about the UV lamp 200. Each flexible finger 510 includes a locking lip or flange 515 located at the distal end of the finger 510. In the illustrated embodiment, the free end of the finger 510 has a T shape and is configured to engage the neck portion 16 and in particular, engage the external threads 15 formed along the neck portion 16 (a radially outermost finger can have an L shape free end). The resiliency of the fingers 510 permit the neck portion 12 to be received within the proper space and then the fingers 510 flex inwardly toward the rest position so as to drive the lip 515 into engagement with the threads (e.g., between two adjacent threads). This results in the neck portion 12 being locked in place within the interior 111 of the apparatus 10 around the UV bulb similar to the embodiment in which the member 300 is used.

In this embodiment, the concentric fingers 510 lock with the threads of the bottle 10 to support and hold the neck portion 12 in place while allowing the bottle 10 to be horizontally disposed within the interior 111 of the apparatus 100.

It will be appreciated that the fingers 510 can, in one embodiment, have an annular shape similar to the seals 310 in which the free ends of the fingers 510 have the locking lips. The locking of the lips 515 with the bottle threads remains the same. When the fingers 510 are not continuous and annular in shape, two sets of fingers 510 can be provided with one set above the bottle (i.e., at a 12 o'clock position) and another set below the bottle (i.e., at a 6 o'clock position).

In this embodiment, the apparatus 100 is constructed to be disposed horizontally along a support surface, such as a kitchen countertop; however, is will be appreciated by one of skill in the art that the teachings of the present invention can be modified to produce a vertical standing apparatus. The depiction of a horizontal apparatus 100 is not limiting of the present invention but merely exemplary.

The operation of the apparatus 100 is now described. After consumption of a liquid product, the container 10 (e.g., water bottle) is inserted into the interior 111 of the housing 110 by lifting open the top section 120 of the housing 110. Since the first end portion 150 is integral to and moves with the top section 120, the interior 111 is accessible not only along the side of the housing 110 but is also accessible at the first end 112 since the first end portion 150 has been moved (pivoted) out of position. This allows direct lateral access of the bottle 10 into the interior 111 of the housing 110. Since the UV lamp 200 is received within the interior of the bottle 10, the bottle 10 must be inserted laterally into the apparatus 100 so as align, receive and capture the UV bulb 200 within the interior of the bottle 10. The neck portion 12 is received first into the interior 111 of the housing 110 and is guided to the member 300 where the neck portion 12 is inserted into the proper track 315 as dictated by the size of the bottle 10 and more particularly, the size of the neck portion 12.

Once the neck portion 12 is securely coupled to the member 300 by being received within one track 315 and sealingly contained between seals 310, the other end of the bottle 10 can be supported by adjusting the riser 400 to its proper position where the bottle 10 rests on the upper edge of the riser 400 and is generally horizontally disposed within the interior 111 of the apparatus 100. In this position, the bottle 10 is securely and horizontally disposed within the interior 111 of the housing 110 with the UV bulb 200 being disposed within the interior of the bottle 10 so that when activated, UV light is emitted along and into contact with the interior surfaces of the bottle 10 for sterilizing thereof.

As discussed herein, the user can select one of a number of operating modes to perform the sterilization. For example, the user can select one of plurality of programmed operating times based on certain characteristics, such as bottle types, etc. The different operating times result in different sterilization processes being employed. In most application, the UV bulb 200 is energized for a period of less than 5 minutes and in particular, the UV bulb 200 is energized for less than 3 minutes. However, these are merely exemplary time periods and it is contemplated that in different applications the time period for treatment may be less or more than the above stated time periods.

In yet another embodiment, the user's selection can also result in a different energy (power) being selected and employed. Alternatively, the user can simply manually select and enter the desired program time for UV emission. This can be down with the switch or other button or by using of a keypad. In the embodiment in which the UV light source does not automatically turn on, the user then manipulates the actuator 192 to turn on the apparatus 100 and energy is delivered to the UV bulb 200. The LED display can show the progress of the treatment (e.g., time remaining) as well as indicate that the UV bulb 200 is activated.

The apparatus 100 can have a safety feature in that in the event that the prematurely opens the cover (top section 120) relative to the bottom section 130, the energy to the UV bulb 200 is terminated. As a result, the user is not exposed to any potentially dangerous UV radiation.

In yet another embodiment, when both the member 300 and riser 400 are employed to hold the bottle 10 at least substantially horizontal within the interior 111, the member 300 can be in the form of concentric arcuate shaped shelves or support walls that extend radially outward from the UV bulb 200 that is located in the center thereof. Thus, unlike the embodiment of FIG. 1, the arcuate shaped shelves are not completely circular (annular) in nature but instead represent and are in the form of only a partial acruate length thereof. The arcuate shaped shelves extend outwardly and downwardly from the UV bulb 200 toward the floor of the bottom section 130. These arcuate shaped shelves thus support the bottom of the neck portion 12 of the bottle 10. Unlike the more active engagement mechanisms of the other embodiments, the neck portion 12 in this embodiment is merely supported on the shelf. The riser 400 in turn and in combination supports the bottle 10 so that it can remain in a horizontal orientation and be spaced from the UV bulb 200 so that it is out of contact therewith.

Each shelf can contain a central ridge or lip that is intended to mate with the threads 15 and in particular, the central ridge can be received between two adjacent threads 15 to form a frictional fit. The central ridge thus at least positions and retains the neck portion 12 on the arcuate shaped shelf. Lateral movement of the bottle 10 is thus prevented.

The bottle 10 can be formed of any conventional plastic that is suitable for use in the present invention and in particular, the bottle 10 can be formed of polyethyleneterphthalate ("PET") bottle or blow molded high density polyethylene ("HDPE"). The bottle 10 can be composed of polyethylene, polypropylene, or copolymers or other suitable material.

The disclosed present invention, which involves the use of ultra violet (UV) light sterilization technology in a portable fashion, exceeds the convenience and requirements of the marketed sterilization units, which use cold water, electrical and/or microwave means to sterilize containers, such as baby feeding equipment and the like. In principle, the use of UV technology to sterilize the inside of a bottle can be viewed as a more efficient and convenient means of killing bacteria and other harmful agents, which may be found on the surfaces of bottle and thereby, encourages reuse of a bottle at least for several times. The disclosed invention has the potential to operate with a host of different shapes and sizes of branded bottles (water bottles), thereby providing an alternative, portable, and universal means of sterilizing bottles.

What is claimed is:

1. An apparatus for sterilizing an inside of a container comprising:
    a housing having a first part and a second part that define an interior, the first part being movable relative to the second part between an open position and a closed position in which the first and second parts are sealed, the housing including a first end portion that closes off a first end of the housing and is attached to the first part such that the first end portion and the first part move in unison between the open and closed positions, the housing also including a second end portion that closes off a second end of the housing and is attached to the second part and remains in a fixed position in the open and closed positions;
    a UV bulb disposed horizontally within the interior and spaced above a floor of the second part;
    a first retaining member for holding a neck portion of the container, the first retaining member being disposed about the UV bulb at one end thereof and having a plurality of concentric slots for accommodating different sized neck portions to permit the UV bulb to be received within an interior of the container;
    a support disposed along the second part, wherein the first retaining member and support are configured to hold the container in an least substantially horizontal orientation within the interior; and
    a power source operatively connected to the UV bulb and to a controller that provides control over the activation of the UV bulb.

2. The apparatus of claim 1, wherein each of the first part and the second part of the housing has a semi-circular shape such that in the closed position, the first and second parts define a cylindrical body.

3. The apparatus of claim 1, wherein the first retaining member comprises a plurality of concentric seal members formed of a resilient material, with one concentric slot being defined a pair of adjacent seal members.

4. The apparatus of claim 3, wherein the seal members are formed of rubber.

5. The apparatus of claim 3, wherein the UV bulb comprises an elongated bulb that is disposed within an inner, centermost seal member.

6. The apparatus of claim 1, wherein each of the first and second end portions comprises an end cap that closes off the housing in the closed position.

7. The apparatus of claim 6, wherein the power source and controller are disposed within the second end portion.

8. The apparatus of claim 1, wherein the first part includes a first sealing edge that seats against and seals relative to a second sealing edge of the second end portion.

9. The apparatus of claim 1, wherein the second part includes a third sealing edge that seats against and seals relative to a fourth sealing edge of the first end portion.

10. The apparatus of claim 1, wherein the support comprises an adjustable riser that supports the bottle and can be locked into one of a plurality of different heights.

11. The apparatus of claim 10, wherein the support comprises a pivotable riser that is pivotally attached to the second section, wherein a top edge of the support comprises an arcuate edge having a concave shape.

12. The apparatus of claim 11, wherein the pivotable riser includes biased locking pins that extend into a pair of openings formed within the second part for locking the riser in place.

13. The apparatus of claim 12, wherein there are a plurality of pairs of openings formed in the second part corresponding to different positions of the riser, wherein the arcuate edge is located at different heights in the different positions.

14. The apparatus of claim 1, wherein the first retaining member comprises a plurality of flexible fingers that define the concentric slots, the flexible fingers being arranged in pairs of opposing flexible fingers, with one pair of the flexible fingers defining one concentric slot.

15. The apparatus of claim 14, wherein each flexible finger comprises a locking flange located at a distal end of the flexible finger.

16. The apparatus of claim 15, wherein the locking flange comprises a T-shaped locking flange for engaging a thread associated with a neck of the bottle.

17. The apparatus of claim 1, wherein the support is movable and can be locked in different positions in which a top edge of the support is at different heights, the different positions of the support corresponding to the different concentric slots such that when the bottle is in one concentric slot, there is a corresponding position for the support to ensure that the bottle remains in a horizontal orientation.

18. The apparatus of claim 1, wherein the UV bulb is positioned for reception within an open neck of the container to allow the UV bulb to be horizontally oriented within the interior of the container.

19. The apparatus of claim 18, wherein a distal end of the UV bulb is disposed between the support and the first retaining member.

20. An apparatus for sterilizing an inside of a container comprising:
a housing having a first part and a second part that define an interior, the first part being movable relative to the second part between an open position and a closed position in which the first and second parts are sealed, the housing including a first end portion that closes off a first end of the housing and is attached to the first part such that the first end portion and the first part move in unison between the open and closed positions, the housing also including a second end portion that closes off a second end of the housing and is attached to the second part and remains in a fixed position in the open and closed positions;
a UV bulb disposed horizontally within the interior and spaced above a floor of the second part;
a first retaining member for holding a neck portion of the container, the first retaining member being disposed about the UV bulb at one end thereof and having a plurality of concentric slots for accommodating different sized neck portions to permit the UV bulb to be received within an interior of the container, wherein the first retaining member comprises a plurality of concentric seal members formed of a resilient material, with one concentric slot being defined a pair of adjacent seal members;
a support disposed along the second part, wherein the first retaining member and support are configured to hold the container in an least substantially horizontal orientation within the interior, wherein the support comprises a pivotable riser that is pivotally attached to the second section, wherein a top edge of the support comprises an arcuate edge having a concave shape; and
a power source operatively connected to the UV bulb and to a controller that provides control over the activation of the UV bulb;
wherein the support is movable and can be locked in different positions in which a top edge of the support is at different heights, the different positions of the support corresponding to the different concentric slots such that when the bottle is in one concentric slot, there is a corresponding position for the support to ensure that the bottle remains in a horizontal orientation.

* * * * *